(12) United States Patent
Gordils Wallis

(10) Patent No.: US 6,347,940 B1
(45) Date of Patent: Feb. 19, 2002

(54) INSTRUMENT AND PROCESS FOR THE MINIMUM DISTANCE VERIFICATION BETWEEN TWO TEETH FOR THE PLACEMENT OF ONE OR TWO BONE INTEGRATED CYLINDRICAL OR SCREWED TYPE IMPLANTS IN DENTISTRY

(76) Inventor: Antonio Jose Gordils Wallis, Av. Francisco de Miranda, Edif. Cavendes, Piso 12, Los Palos Grandes, Caracas-Venezuela, Apartado 68.606, Caracas 1062 (VE)

(*) Notice: Subject to any disclaimer, the term of this patent is extended or adjusted under 35 U.S.C. 154(b) by 0 days.

(21) Appl. No.: 09/643,406
(22) Filed: Aug. 22, 2000
(51) Int. Cl.[7] ................................. A61C 19/04
(52) U.S. Cl. ..................... 433/72; 433/76; 606/96; 33/513
(58) Field of Search .................... 433/72, 74, 76, 433/141; 33/513; 606/96

(56) References Cited

U.S. PATENT DOCUMENTS

| 2,634,501 | A | * | 4/1953 | Linet | |
| 5,030,219 | A | * | 7/1991 | Matsen, III et al. | 606/96 |
| 5,112,336 | A | * | 5/1992 | Krevolin et al. | 606/96 |
| 5,700,267 | A | * | 12/1997 | Urbanski | 606/96 |
| 5,769,856 | A | * | 8/1998 | Dong et al. | 606/96 |
| 5,888,065 | A | * | 3/1999 | Sussman | 433/76 |
| 6,123,546 | A | * | 9/2000 | Bergström et al. | 433/72 |
| 6,143,012 | A | * | 11/2000 | Gausepohl | 606/96 |

* cited by examiner

Primary Examiner—Ralph A. Lewis
(74) Attorney, Agent, or Firm—Ladas & Parry

(57) ABSTRACT

An instrument has a sheet which has a centered perforation joined by an extension to another larger sheet which has two perforations and, from the larger sheet, an extension joining it to handle for a process verifying space between teeth.

4 Claims, 3 Drawing Sheets

I

IV

II

V

III

VI

INSTRUMENT AND PROCESS FOR THE MINIMUM DISTANCE VERIFICATION BETWEEN TWO TEETH FOR THE PLACEMENT OF ONE OR TWO BONE INTEGRATED CYLINDRICAL OR SCREWED TYPE IMPLANTS IN DENTISTRY

FIELD OF INVENTION

This invention confirms that the edentuious space between teeth has the minimum distance necessary for the placement of one or two implant.

This invention confirms that the first and second marks were the implants are to be placed have the minimum distance amongst them and with the neighboring teeth.

This invention provides a visual guide to determine the relation between the diameter of an implant and the alveolar rim.

This invention centralizes the distance between two teeth for the implant placement.

BACKGROUND

In many cases the distance between two teeth can be insufficient for one or two implants, which could generate an exaggerated proximity between the implant (s) and the neighboring teeth, obstructing the prosthetic restoration and creating hygiene problems which may compromise the case prognosis.

They are small titanium cylinders that behave as an artificial root, and they may provide:

- a method to anchor total upper and lower removable prosthetics;
- a method to place total or partial fixed prosthetics; and
- a method to replace a single tooth.

STEP-BY-STEP CLINICAL PROCEDURES a) Pre-Medication
b) Anesthesia
c) Elevation of the total thickness flap
d) Placement of the surgical splint
e) Marking of the implant location
f) Use of Pilot Drill
g) Use of progressive diameter drills until reaching the diameter of the selected implant
h) Placement of the implant
i) Second surgical phase for the placement of healing devices once the bone integration period has elapsed.

To these ends, an instrument has a sheet which has a centered perforation joined by an extension to another larger sheet which has two perforations and, from the larger sheet, an extension joining it to handle for a process verifying space between teeth.

BRIEF DESCRIPTION OF THE DRAWINGS

FIGS. 1 and 2 show the instrument of the invention. FIG. 3 shows the use of the invention.

FIG. 3 shows the use of the invention Instrument

FIG. 3 (I) shows the edentulous space (9) between two teeth where the implant will be placed.

FIG. 3(II) shows the sheet of a perforation (1) is located in the edentulous space (9) between two teeth and the minimum adequate distance is verified for the placement of the implants.

FIG. 3(III) with a round drill (10) through the perforation (2) the bone is market achieving and equidistant distribution of the edentulous space.

FIG. 3(IV) edentulous space (11) between two teeth where the implants will be placed.

FIG. 3(V) the sheet with two perforations (4) is placed in the edentulous space (11) between the teeth and the minimum adequate distance is verified for the placement of the two implants.

FIG. 3 (VI) with a round drill (10) through the perforations (5) and (6) the bone is marked achieving and equidistant distribution of the endentulous space.

Figure 1:
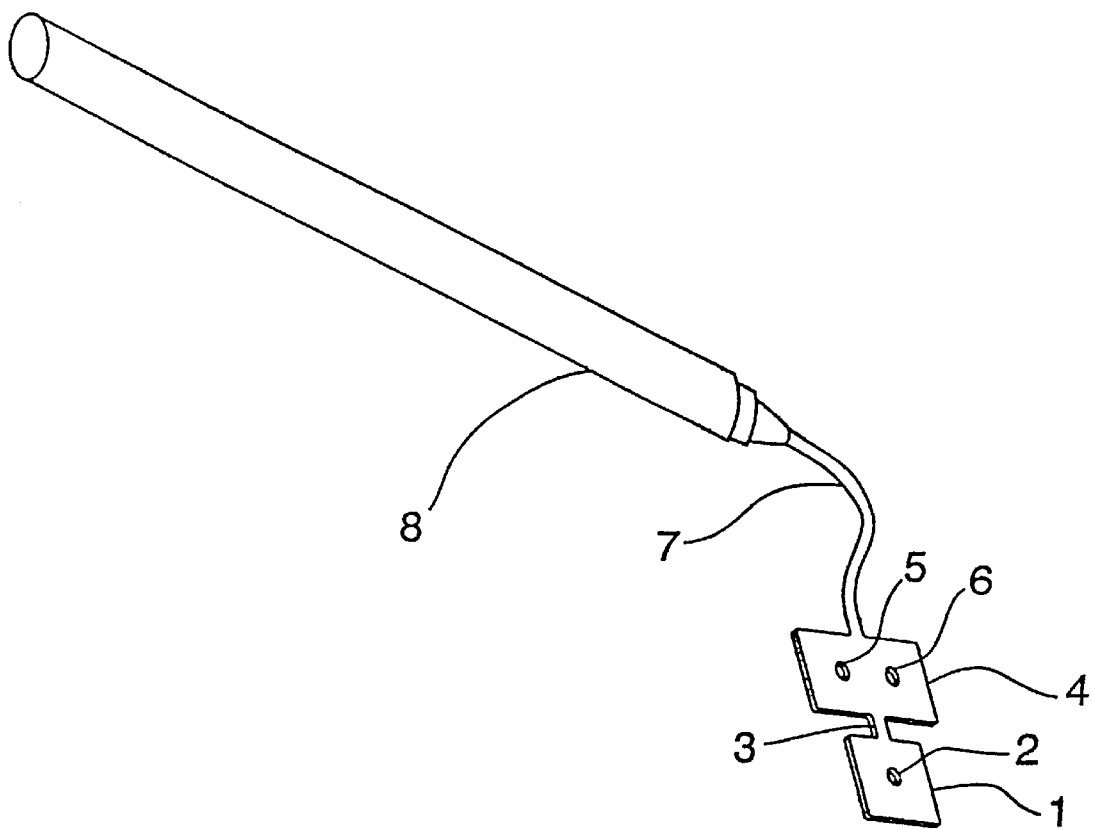
FIG. 1 is a perspective view of the invention Instrument
Figure 2:
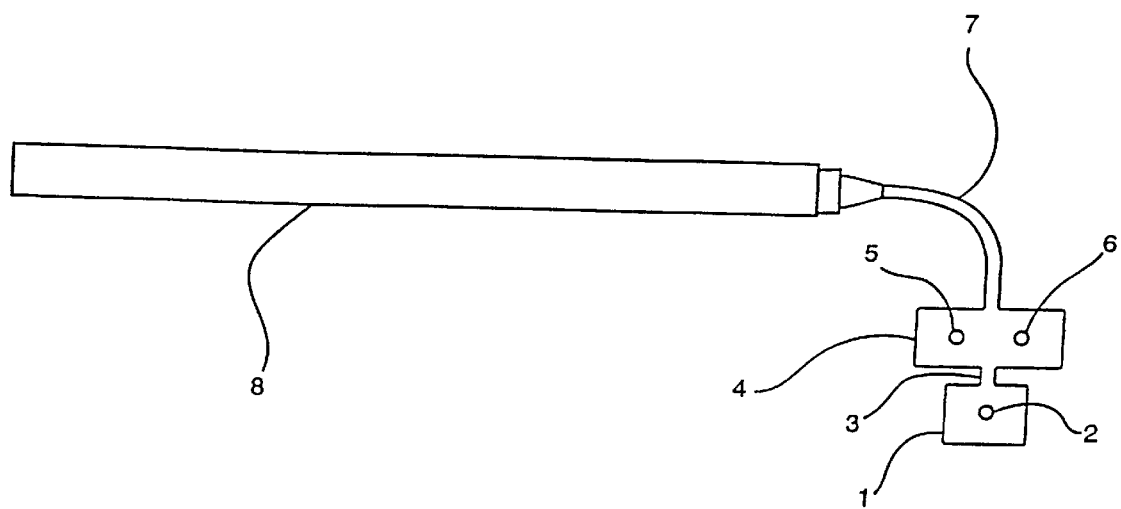
FIG. 2 is an elevational view of the Instrument
Figure 3:
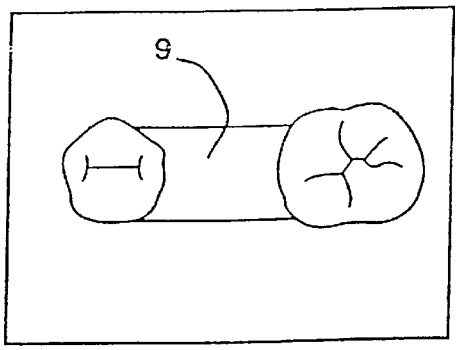
FIG. 3 is a schematic sequence showing the procedure steps for which the Instrument is used.
Figure 3:
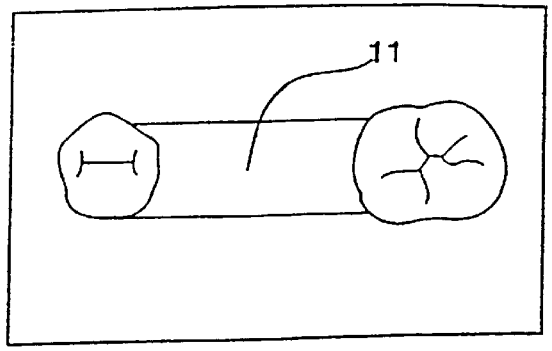
Figure 3:
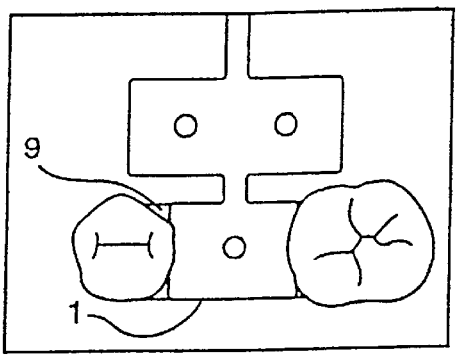
Figure 3:
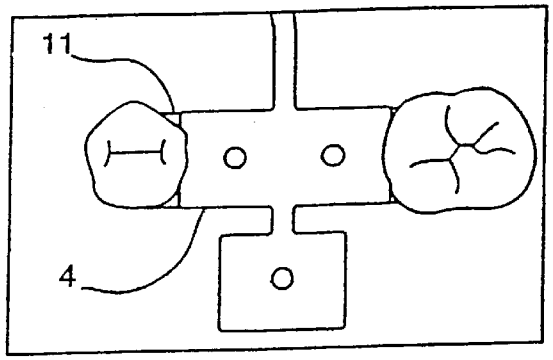
Figure 3:
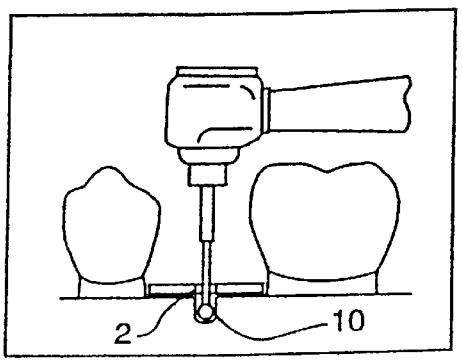
Figure 3:
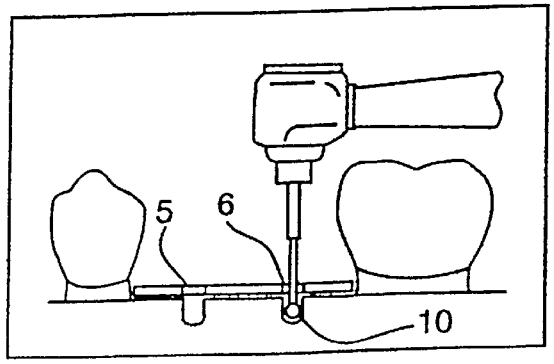

What is claimed is:

1. An Instrument which verifies whether the distance between two teeth is the minimum adequate distance for the placement of one or two implants, verifies that marks made with a surgical splint have amongst them the minimum adequate distance, and centers edentulous space for placement of an implant or divides equidistantly the space for the placement of two implants, the instrument comprising:

a rectangular sheet with a central perforation joined by an extension to another rectangular sheet larger than the aforementioned with two perforations from which a handle extends.

2. A process to verify a minimum distance of edentulous space between two teeth for placement of one or two cylindrical or screwed type dental implants comprising:

(i) to locate an implant, placing a first sheet with a single perforation between the two teeth in super-position on the edentulous space, whereby if the size of the first sheet is equal to or less than the distance between the two teeth, it will be possible to place the implant, or if the size of the first sheet is greater than the distance between the two teeth, the distance will not permit placement of the implant; or (ii) to locate two implants, placing a second sheet with two perforations between the two teeth in super-position on the edentulous space, whereby if the size of the second sheet is equal to or less than the distance between the two teeth, it will be possible to place the two implants, or if the size of the second sheet is greater than the distance between the two teeth, the second distance will not permit placement of the two implants.

3. A process to center location of an implant, to divide equidistantly edentulous space for location of two implants and verify minimum distance between two implants, said process comprising the steps of:

(i) for location of the implant, placing a first sheet with a single perforation sheet between two teeth and, with a round drill marking the edentulous space through the single perforation;

(ii) for dividing equidistantly the edentulous space for the location of the two implants, placing a second sheet with two perforations between the two teeth and, with a round drill marking the edentulous space through the two perforations; and (iii) for verifying the minimum distance between the two implants, superimposing the second sheet on marks made at the edentulous space with a surgical splint, and if a distance between the two perforations of the second sheet coincides with or is smaller than a distance between the marks, the minimum distance is adequate for the second sheet, or if the distance between the two perforations of the second sheet is greater than the distance between the marks, the minimum distance will be insufficient to place the two implants.

4. A process to verify correspondence of bone rim to diameter of a selected implant comprising:

placing a sheet with one or two perforations on the bone rim and visually determining a ratio between a width of the sheet and a width of the bone rim in order to verify if the diameter of the selected implant corresponds to a width of the bone rim.

* * * * *